United States Patent
Dong et al.

(10) Patent No.: US 11,259,868 B2
(45) Date of Patent: *Mar. 1, 2022

(54) CORRUGATED RADIOFREQUENCY ABLATION CATHETER AND APPARATUS THEREOF

(71) Applicant: SHANGHAI GOLDEN LEAF MED TEC CO., LTD., Shanghai (CN)

(72) Inventors: Yonghua Dong, Shanghai (CN); Meijun Shen, Shanghai (CN)

(73) Assignee: SHANGHAI GOLDEN LEAF MED TEC CO., LTD., Shanghai (CN)

(*) Notice: Subject to any disclaimer, the term of this patent is extended or adjusted under 35 U.S.C. 154(b) by 1035 days.

This patent is subject to a terminal disclaimer.

(21) Appl. No.: 15/573,461

(22) PCT Filed: May 10, 2016

(86) PCT No.: PCT/CN2016/081620
§ 371 (c)(1),
(2) Date: Nov. 11, 2017

(87) PCT Pub. No.: WO2016/180326
PCT Pub. Date: Nov. 17, 2016

(65) Prior Publication Data
US 2018/0104002 A1    Apr. 19, 2018

(30) Foreign Application Priority Data

May 13, 2015  (CN) .......................... 201510243653.7
Aug. 12, 2015  (CN) .......................... 201510492530.7
Aug. 12, 2015  (CN) .......................... 201520604993.3

(51) Int. Cl.
*A61B 18/14*    (2006.01)
*A61B 18/12*    (2006.01)
(Continued)

(52) U.S. Cl.
CPC .......... *A61B 18/1492* (2013.01); *A61B 18/12* (2013.01); *A61B 18/1206* (2013.01);
(Continued)

(58) Field of Classification Search
CPC ................ A61B 18/1492; A61B 18/18; A61B 2017/00323; A61B 2017/00331;
(Continued)

(56) References Cited

U.S. PATENT DOCUMENTS

| | | | |
|---|---|---|---|
| 5,095,915 A * | 3/1992 | Engelson | A61M 25/09 600/434 |
| 5,687,723 A * | 11/1997 | Avitall | A61B 5/6855 600/374 |
| 5,782,828 A | 7/1998 | Chen et al. | |
| 6,745,080 B2 * | 6/2004 | Koblish | A61B 18/1492 607/122 |
| 9,629,982 B2 | 4/2017 | Caples et al. | |

(Continued)

FOREIGN PATENT DOCUMENTS

| | | |
|---|---|---|
| CN | 101309651 A | 11/2008 |
| CN | 104095679 A | 10/2014 |

(Continued)

*Primary Examiner* — Ronald Hupczey, Jr.
(74) *Attorney, Agent, or Firm* — Soroker Agmon Nordman

(57) ABSTRACT

A corrugated radiofrequency ablation catheter and an apparatus thereof. The radiofrequency ablation catheter is provided with a strip-shaped connecting catheter (10). An electrode frame is provided at the front extremity of the connecting catheter (10). A control handle (20) is provided at the rear extremity of the connecting catheter (10). The electrode frame is a corrugated electrode frame consisting of one or more corrugations. One or more electrodes (2) respectively are distributed on the corrugations. Slidable, supporting, wall-attaching adjustment wires (6) are provided within one lumen of the connecting catheter (10) and the electrode frame. The supporting, wall-attaching adjustment (Continued)

wires (6) are divided into a flexible segment (61) away from the control handle and a rigid segment (62) in proximity to the control handle.

10 Claims, 11 Drawing Sheets

(51) Int. Cl.
 *A61N 1/06* (2006.01)
 *A61B 18/00* (2006.01)
(52) U.S. Cl.
 CPC .......... *A61B 18/14* (2013.01); *A61B 18/1477* (2013.01); *A61N 1/06* (2013.01); *A61B 2018/00404* (2013.01); *A61B 2018/00577* (2013.01); *A61B 2018/00791* (2013.01); *A61B 2018/00875* (2013.01)
(58) Field of Classification Search
 CPC .......... A61B 2018/00434; A61B 2018/00577; A61B 2018/0094; A61B 2018/1465; A61M 25/0138
 See application file for complete search history.

(56) References Cited

U.S. PATENT DOCUMENTS

| | | | |
|---|---|---|---|
| 2001/0020174 A1* | 9/2001 | Koblish | A61B 18/1492 606/194 |
| 2005/0010095 A1 | 1/2005 | Stewart et al. | |
| 2011/0004157 A1* | 1/2011 | Dewaele | A61M 25/0158 604/95.01 |
| 2012/0157992 A1 | 6/2012 | Smith | |
| 2013/0231659 A1 | 9/2013 | Hill et al. | |
| 2013/0304061 A1* | 11/2013 | Chang | A61B 18/1492 606/41 |
| 2017/0027640 A1 | 2/2017 | Kunis et al. | |
| 2017/0049512 A1 | 2/2017 | Chang et al. | |

FOREIGN PATENT DOCUMENTS

| | | |
|---|---|---|
| CN | 104159536 A | 11/2014 |
| CN | 104257426 A | 1/2015 |
| CN | 104271063 A | 1/2015 |
| CN | 104605930 A | 5/2015 |
| CN | 105125281 A | 12/2015 |
| CN | 205019160 U | 2/2016 |
| EP | 2609886 A2 | 7/2013 |

* cited by examiner

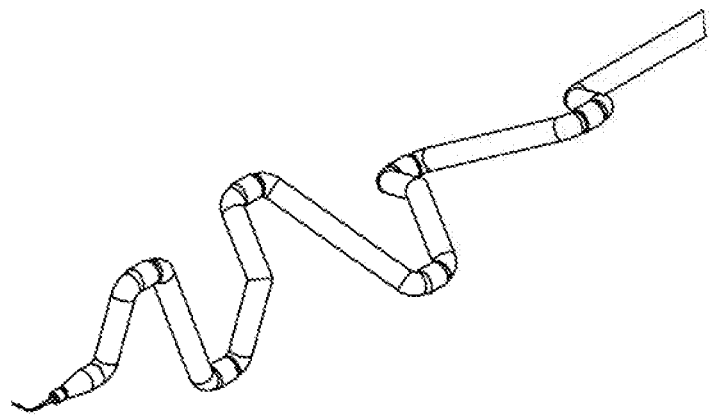 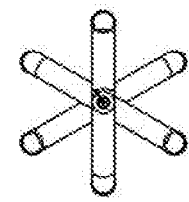
FIG. 9A  FIG. 9B
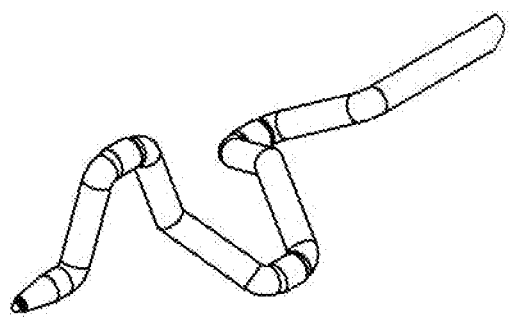 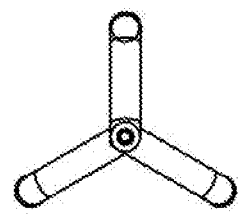
FIG. 10A  FIG. 10B
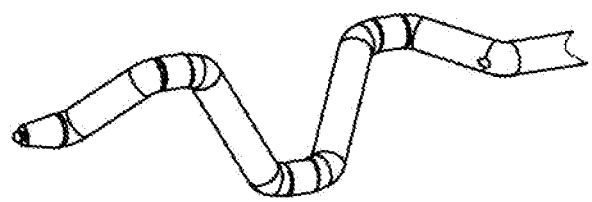 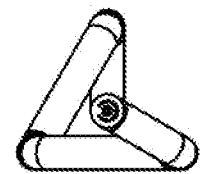
FIG. 11A  FIG. 11B

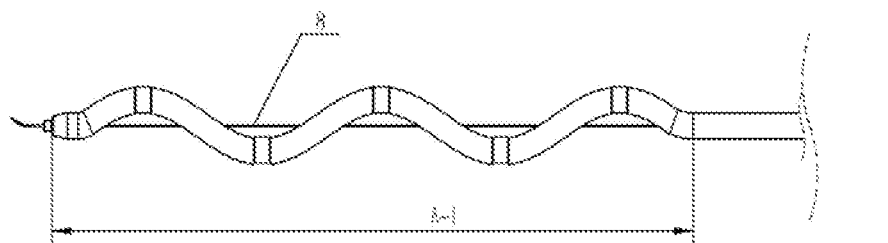 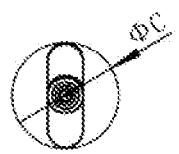
FIG. 12A          FIG. 12B
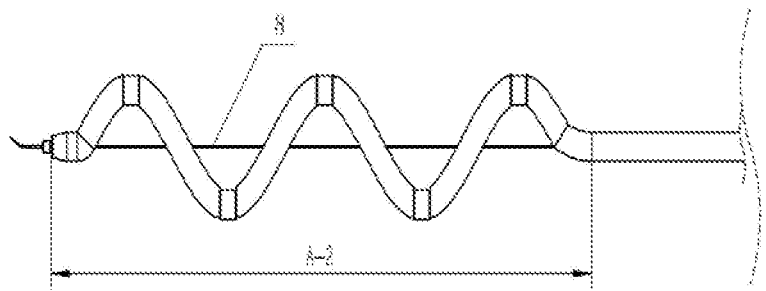 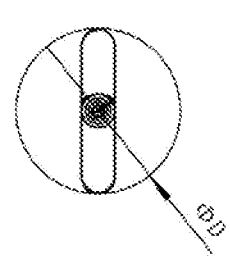
FIG. 13A          FIG. 13B
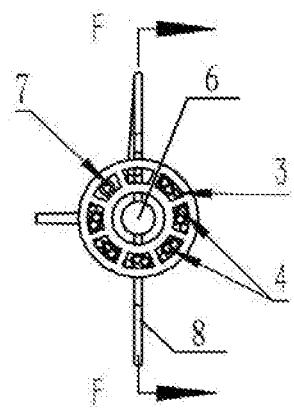
FIG. 14

CORRUGATED RADIOFREQUENCY ABLATION CATHETER AND APPARATUS THEREOF

TECHNICAL FIELD

The present invention relates to a corrugated radiofrequency ablation catheter, also relates to a radiofrequency ablation apparatus comprising the radiofrequency ablation catheter, and belongs to the technical field of interventional medical instruments.

RELATED ART

In a radiofrequency ablation system, a radiofrequency ablation catheter is a key device used for human blood vessel intervention and radiofrequency energy release. Radiofrequency electrodes are installed on a frame at the front extremity of the radiofrequency ablation catheter, the frame is used for bearing the radiofrequency electrodes, and the frame expands to be attached to the wall before radiofrequency starts and retracts after radiofrequency ends. Since radiofrequency ablation surgery is conducted through direct human blood vessel intervention, the expanding and retracting size of the frame needs to be matched with the diameters of human blood vessels.

The diameters of human blood vessels vary with ablation portions. Besides, the diameters of human blood vessels vary from person to person. For example, the renal artery diameters of different persons range from 2 mm to 12 mm, showing a great difference. In the prior art, the expanding and retracting size of the electrode end of the radiofrequency ablation catheter is generally fixed and can not adapt to different diameters of human blood vessels, thus being small in coverage over human blood vessels with different diameters. Therefore, when radiofrequency ablation surgery is conducted on different patients, radiofrequency ablation catheters of different specifications and models are usually required for ablation. Even so, the problem that radiofrequency electrodes can not be attached to the wall at the same time still exists during certain surgery, and the surgical effect is influenced.

Radiofrequency ablation catheters can be of various structures based on the shape of electrodes and the shape of an electrode frame, such as a balloon type, a puncture needle type, a spiral type and a lobe structure. The adaptability of all existing radiofrequency ablation catheters to blood vessels with different diameters is limited.

SUMMARY

The primary technical problem to be solved by the present invention is to provide a corrugated radiofrequency ablation catheter.

Another technical problem to be solved by the present invention is to provide a radiofrequency ablation apparatus comprising the radiofrequency ablation catheter.

In order to achieve the above-mentioned purposes, the present invention adopts the following technical scheme:

the corrugated radiofrequency ablation catheter is provided with a strip-shaped connecting catheter, an electrode frame is provided at the front extremity of the connecting catheter, and a control handle is provided at the rear extremity of the connecting catheter;

wherein the electrode frame is a corrugated electrode frame consisting of one or more corrugations, where one or more electrodes are distributed on the corrugations;

a slidable, supporting, wall-attaching adjustment wire is provided within one lumen of the electrode frame and the connecting catheter, and the supporting, wall-attaching adjustment wire is divided into a flexible segment away from the control handle and a rigid segment in proximity to the control handle; the head end of the supporting, wall-attaching adjustment wire is limited outside the front extremity of the electrode frame, and can slide relative to the front extremity of the electrode frame; the tail end of the supporting, wall-attaching adjustment wire is fixed to a control element arranged on the control handle or arranged externally, and the control element is used for controlling the supporting, wall-attaching adjustment wire to move forward and backward;

when the rigid segment of the supporting, wall-attaching adjustment wire is in the electrode frame, the portion, which overlaps with the rigid segment, of the electrode frame tends to be linear; and when the flexible segment of the supporting, wall-attaching adjustment wire is in the electrode frame, the portion, which overlaps with the flexible segment, of the electrode frame tends to be corrugated.

Preferably, the flexible segment is made of a filament with diameter or rigidity smaller than that of the rigid segment, and the flexible segment and the rigid segment are integrally formed or assembled by means of two filaments with different diameters.

Or, preferably, the flexible segment is of a spring structure or a hose structure.

Or, preferably, the flexible segment and the rigid segment of the supporting, wall-attaching adjustment wire are made of one piece of rigid material, wherein the front segment of the material is provided with grooves and/or holes so as to form the flexible segment; or the flexible segment and the rigid segment of the supporting, wall-attaching adjustment wire are made of one piece of flexible material, wherein the rigid segment is formed by assembling an outer sleeve on the rear segment.

Preferably, the corrugation is in the shape of a fold line composed of several straight line segments, or is composed of several curve segments, or is composed of curves and straight lines.

Preferably, the electrodes are arranged at the crests/troughs of the corrugations.

Preferably, a developing head and/or soft guide wire is provided at the head end of the supporting, wall-attaching adjustment wire.

Preferably, the corrugated radiofrequency ablation catheter further comprises a shaping wire provided within the electrode frame.

Preferably, a wall-attaching adjustment wire is further arranged, the rear segment of the wall-attaching adjustment wire is slidably provided within one lumen of the connecting catheter, and the rear extremity of the wall-attaching adjustment wire is connected to the control element arranged on the control handle or arranged externally; the front segment of the wall-attaching adjustment wire protrudes to the outside of the electrode frame and either runs through one or more holes provided on the corrugations or runs around the multiple corrugations, and then the front extremity returns to the interior of the electrode frame to be fixed.

Or, preferably, a wall-attaching adjustment wire is further arranged, the wall-attaching adjustment wire is composed of two or more filaments, the multiple filaments are used for adjusting one corrugation or one segment of corrugations on the electrode frame respectively, one segment of corrugations comprises two or more corrugations, the front extremity of each filament is fixed to one end of the corresponding corrugation/corrugated segment, and the other extremity of each filament runs around the corresponding corrugation/corrugated segment, runs through the lumen in the electrode frame and the connecting catheter, and is then fixed to the corresponding control element provided on the control handle or arranged externally.

The radiofrequency ablation apparatus comprises the radiofrequency ablation catheter, and a radiofrequency ablation main unit connected with the radiofrequency ablation catheter.

According to the corrugated radiofrequency ablation catheter, by improving the structure of the supporting, wall-attaching adjustment wire, the diameter of a corrugated segment of the catheter can be changed without the aid of other apparatus. On one hand, by controlling the rigid segment of the supporting, wall-attaching adjustment wire to overlap with the electrode frame, the diameter of the corrugated segment can be reduced, the length becomes larger, and the corrugated segment tends to be linear so as to adapt to a catheter guide tube/sheath; on the other hand, when the supporting, wall-attaching adjustment wire is pulled back to enable the flexible segment to overlap with the electrode frame, the electrode frame can recover to be corrugated. According to the corrugated radiofrequency ablation catheter, by controlling different portions (the flexible segment, the rigid segment, or part of the flexible segment and part of the rigid segment) of the supporting, wall-attaching adjustment wire to overlap with the electrode frame, the form of the electrode frame can be changed, thus significantly reducing the difficulty of the radiofrequency ablation catheter in entering the catheter guide tube/sheath, also greatly facilitating movements of the corrugated electrode frame in a target lumen, and allowing facilitated operation and a simple structure.

BRIEF DESCRIPTION OF THE DRAWINGS

FIG. 9A and FIG. 9B are a three-dimensional structure diagram and a side view of a corrugated radiofrequency ablation catheter in the second embodiment respectively;

FIG. 10A and FIG. 10B are a three-dimensional structure diagram and a side view of a corrugated radiofrequency ablation catheter in the third embodiment respectively;

FIG. 11A and FIG. 11B are a three-dimensional structure diagram and a side view of a corrugated radiofrequency ablation catheter in the fourth embodiment respectively;

FIG. 12A and FIG. 12B are a three-dimensional structure diagram and a side view of a corrugated radiofrequency ablation catheter in the fifth embodiment respectively;

FIG. 13A and FIG. 13B are a three-dimensional structure diagram and a side view of the corrugated radiofrequency ablation catheter which retracts under the action of a wall-attaching adjustment wire in the fifth embodiment respectively;

FIG. 14 is a section view of an electrode frame of the radiofrequency ablation catheter shown in the fifth embodiment;

DETAILED DESCRIPTION

The technical content of the present invention is further described in detail with reference to accompanying drawings and specific embodiments.

First Embodiment

Figure 3:
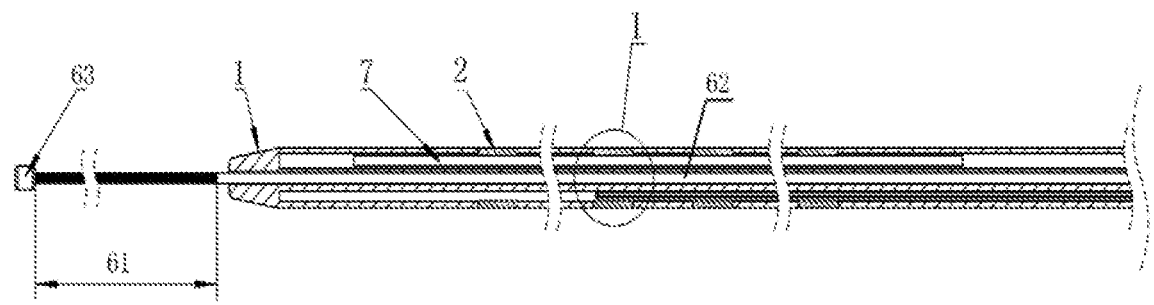
FIG. 3 is a D-D cross section view of the corrugated radiofrequency ablation catheter when a rigid segment of a supporting, wall-attaching adjustment wire overlaps with the electrode frame.
Figure 4:
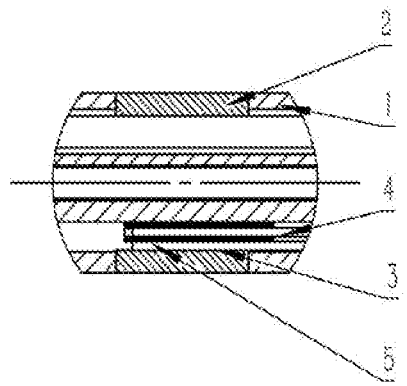
FIG. 4 is a local enlarged view of a portion I of the corrugated radiofrequency ablation catheter shown in FIG. 3.
Figure 5A:
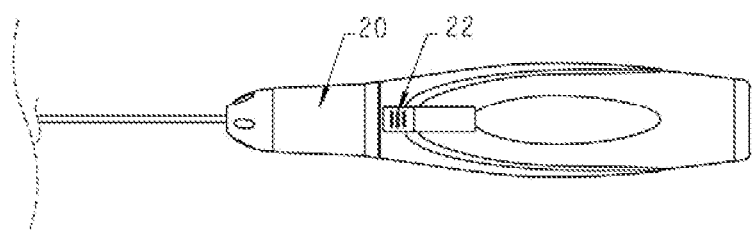
FIG. 5A is a state view of a control handle when a button control element moves forward for wire feeding and the rigid segment of the supporting, wall-attaching adjustment wire overlaps with the electrode frame.
Figure 5B:
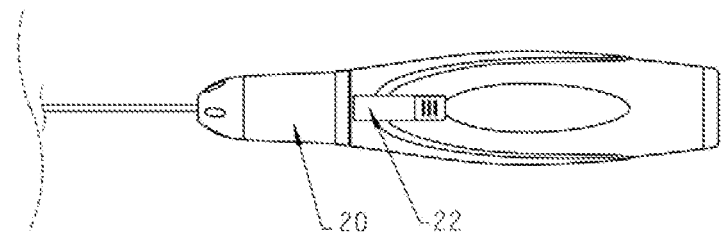
FIG. 5B is a state view of the control handle when the button control element moves backward for wire pulling and the flexible segment of the supporting, wall-attaching adjustment wire overlaps with the electrode frame.

It can be learnt from FIG. 1A to FIG. 5B that a corrugated radiofrequency ablation catheter provided by the present invention comprises a strip-shaped connecting catheter 10, a corrugated electrode frame is provided at the front extremity of the connecting catheter 10 (see FIG. 1A), and a control handle 20 is provided at the rear extremity of the connecting catheter 10 (see FIG. 5A and FIG. 5B). During actual manufacturing, the electrode frame can be manufactured integral with the connecting catheter 10, the connecting frame is the part configured to be corrugated at the front extremity of the connecting catheter 10, and the electrode frame can also be independently manufactured and then connected with the connecting catheter 10 into a whole.

Figures 1A, 1B:
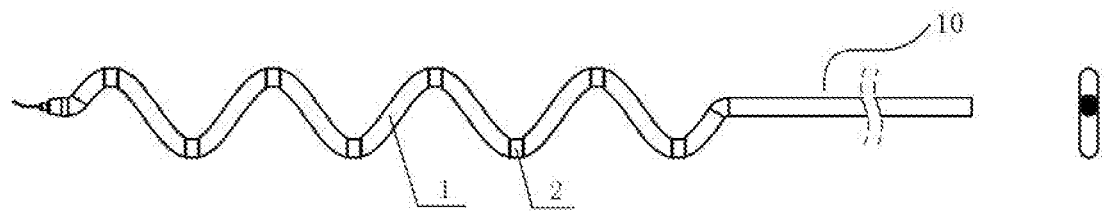
FIG. 1A is a structure diagram of a corrugated radiofrequency ablation catheter.
FIG. 1B is a side view of the corrugated radiofrequency ablation catheter shown in FIG. 1A.

As shown in FIG. 1A, the corrugated electrode frame comprises an outer tube 1 and one or more electrodes 2 provided on the outer tube 1. The outer tube 1 is configured to be a corrugated shape consisting of one or more corrugations; each corrugation can be in the shape of a fold line composed of several straight line segments, such as a triangular wave; each corrugation can also be composed of several curve segments, such as a sine wave or an arc wave; and, each corrugation can also be composed of curves and straight lines, such as a trapezoidal wave with a corner. Besides, the corrugations can also be in other corrugated shapes. Furthermore, in the same electrode frame, the multiple corrugations can be in the same shape and same size, and can also be in different shapes and different sizes. Detailed explanation will be given with reference to specific embodiments. The multiple corrugations of the corrugated electrode frame can be located in different planes and can also be located in the same plane. In the first embodiment, all the corrugations are located in the same plane, and the multiple electrodes 2 are distributed on the corrugations respectively, preferably, the electrodes 2 are arranged at the crests or troughs of the corrugations. The electrodes 2 can be block type electrodes or annular electrodes embedded in the outer periphery of the outer tube 1, the external surfaces of the electrodes 2 can be flush with the external surface of the outer tube 1 or slightly higher than the external surface of the outer tube 1, and the external surfaces of the electrodes 2 can also be lower than the external surface of the outer tube 1.

It can be learnt from the side view as shown in FIG. 1B that in the first embodiment, the corrugations of the corrugated electrode frame are located in the same plane, and the multiple electrodes 2 are arranged at the crests and the troughs respectively. However, in other embodiments to be mentioned below, the multiple corrugations of the corrugated electrode frame can also be distributed in different planes, when the corrugations intersect with one another at the same angel, the profile projections of the multiple electrodes on the electrode frame can be evenly distributed in the circumferential direction, in other words, the profile projections of the multiple electrodes are distributed into an approximate circle on the outer periphery of a target lumen. Of course, when the crossing angles of the corrugations are different, the profile projections, on the electrode frame, of the multiple electrodes 2 can be distributed unevenly in the circumferential direction. Besides, when the electrode frame is long, the multiple corrugations, in the length direction, of the electrode frame can be repeated regularly or randomly, so that the profile projections, on the electrode frame, of the multiple electrodes 2 can overlap.

Figure 2:
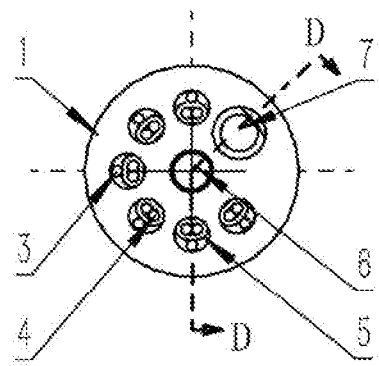
FIG. 2 is a section view of an electrode frame of the corrugated radiofrequency ablation catheter shown in FIG. 1A.

It can be learnt from internal section views as shown in FIG. 2, FIG. 3 and FIG. 4 that the outer tube 1 of the electrode frame can be a single-lumen tube or a multi-lumen tube, and the outer tube 1 can be made of a polymer material or a metal material, such as stainless steel or memory alloy. The outer tube 1 can be machined from straight tubing and bars, and can also be made of a pre-fabricated corrugated special-shaped tube. As shown in FIG. 2, when the outer tube 1 is a multi-lumen tube, multiple lumens are provided inside the outer tube 1 of the electrode frame besides a central lumen, and a set of radiofrequency cables 3 and thermocouple wires 4 is arranged in part of the lumens; the head ends of each set of radiofrequency cables 3 and thermocouple wires 4 are arranged in a single electrode 2, wherein the head ends of the radiofrequency cables 3 are tightly fixed to the electrode 2 through welding, conductive adhesive gluing or other techniques, and the head ends of the two thermocouple wires 4 are welded and coated with thermocouple wire head end insulating layers 5, and then insulated from the radiofrequency cables 3 and the electrode 2.

As shown in FIG. 2, in the present embodiment, a shaping wire 7 is further arranged in one lumen of the outer tube 1, and the shaping wire 7 is fixed in a deformation segment of the electrode frame to be used for supporting the corrugated shape of the electrode frame. Of course, the electrode frame can also be directly shaped into a corrugated shape, so that the shaping wire 7 can be omitted, for example, when the outer tube is made of memory alloy or a polymer material, the outer tube can be directly shaped, so that the shaping wire 7 can be omitted.

As shown in FIG. 2, lumens used for accommodating the supporting, wall-attaching adjustment wire 6 are provided within the electrode frame and the connecting catheter 10 respectively, the supporting, wall-attaching adjustment wire 6 is arranged in the corresponding lumens of the electrode frame and the connecting catheter, the supporting, wall-attaching adjustment wire 6 can slide forward and backward in the corresponding lumens of the electrode frame and the connecting catheter, and the lumens used for accommodating the supporting, wall-attaching adjustment wire 6 can be central lumens of the electrode frame and the connecting catheter and can also be one of multiple lumens distributed around the center. As shown in FIG. 3, the head end of the supporting, wall-attaching adjustment wire 6 is limited outside the front extremity of the electrode frame and can slide relative to the front extremity of the electrode frame, and a developing head 63 is arranged at the head end of the supporting, wall-attaching adjustment wire 6; the tail end of the supporting, wall-attaching adjustment wire 6 runs through the central lumen of the connecting catheter 10 or other lumens and is fixed to the control handle 20, and the control handle 20 is used for controlling the supporting, wall-attaching adjustment wire 6 to move forward and backward.

As shown in FIG. 5A and FIG. 5B, a button control element 22 is arranged on the control handle 20, the tail end of the supporting, wall-attaching adjustment wire 6 is fixed to the button control element 22, and by adjusting the position of the button control element 22 on the control handle 20, the supporting, wall-attaching adjustment wire 6 is controlled to move forward and backward.

Figure 6:
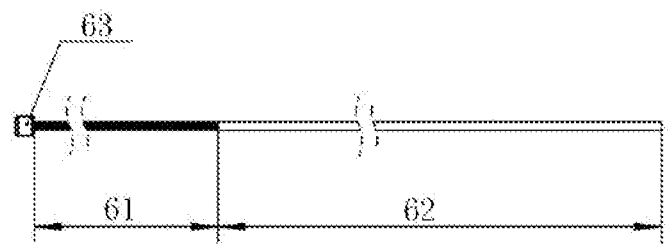
FIG. 6 is a structure diagram of a first supporting, wall-attaching adjustment wire of the present invention.

According to the corrugated radiofrequency ablation catheter, by improving the structure of the supporting, wall-attaching adjustment wire 6, diameter change of the electrode frame is realized without the aid of a catheter guide tube/sheath, and the electrode frame tends to be linear, so that the electrode frame can be easily inserted into the catheter guide tube/sheath and the target lumen; meanwhile, after reaching the target lumen, the electrode frame can recover to be corrugated by pulling back the supporting, wall-attaching adjustment wire 6. Specifically, as shown in FIG. 6, in the radiofrequency ablation catheter, the supporting, wall-attaching adjustment wire 6 is provided with a flexible segment 61 (in proximity to the head end) away from the control handle 20 and a rigid segment 62 (in proximity to the tail end) in proximity to the control handle 20; preferably, the length of the flexible segment 61 is not smaller than the length of the outer tube 1 of the electrode frame, of course, in particular cases, the length of the flexible segment 61 can also be smaller than the length of the outer tube 1 of the electrode frame. By changing the overlapping area of the supporting, wall-attaching adjustment wire 6 and the electrode frame through the control handle 20, the diameter of the corrugated segment of the electrode frame can be changed.

As shown in FIG. 5A and FIG. 3, when the supporting, wall-attaching adjustment wire 6 is pushed forward, the supporting, wall-attaching adjustment wire 6 moves forward to make the rigid segment 62 stay in the electrode frame and the flexible segment 61 exposed from the front extremity of the electrode frame, the corrugated shape of the electrode frame becomes smaller in diameter and larger in length and tends to be linear under the action of the rigid segment 62 of the supporting, wall-attaching adjustment wire 6; ideally, the electrode frame can be linear as shown in FIG. 3. As shown in FIG. 5B, when the supporting, wall-attaching adjustment wire 6 is pulled backward, the supporting, wall-attaching adjustment wire 6 moves backward to make the electrode frame bend gradually as the flexible segment 61 enters the electrode frame, and the electrode frame recovers to be corrugated till only the flexible segment 61 is in the electrode frame and the rigid segment 62 is not (see FIG. 1A). Of course, it also works when part of the flexible segment 61 overlaps with the front segment of the electrode frame and part of the rigid segment 62 overlaps with the rear segment of the electrode frame, in this case, the area, which overlaps with the flexible segment, of the front segment of the electrode frame recovers to be corrugated and the area, which overlaps with the rigid segment, of the rear segment of the electrode frame still tends to be linear. By making the multiple corrugations have different diameters through design, and then controlling the overlapping area between the rigid segment 62 of the supporting, wall-attaching adjustment wire 6 and the corrugated electrode frame, wall attaching of the corrugated electrode frame can be achieved in blood vessels with different diameters. In other words, in the radiofrequency ablation catheter, by controlling the supporting, wall-attaching adjustment wire 6 to move forward so that the rigid segment 62 can overlap with the outer tube 1 of the electrode frame, the diameter of the corrugated segment of the electrode frame can be reduced so as to allow the electrode frame to enter the catheter guide tube/sheath or the target lumen; meanwhile, after the electrode frame enters the target lumen, by pulling the supporting, wall-attaching adjustment wire 6 backward, the flexible segment 62 overlaps with the outer tube 1 of the electrode frame, so that the electrode frame recovers to be corrugated and can be attached to the wall. The position of the button control element 22 on the control handle 20 is shown in FIG. 5A and FIG. 5B; when the button control element 22 moves to the left position, the flexible segment 61 is exposed outwards, and the rigid segment 62 overlaps with the outer tube 1 of the electrode frame; when the button control element 22 moves to the right position, the flexible segment 61 of the supporting, wall-attaching adjustment wire 6 overlaps with the outer tube 1 of the electrode frame.

After the electrode frame naturally expands to be attached to the wall, by further pulling the supporting, wall-attaching adjustment wire 6, the wall attaching condition of the electrodes 2 can be adjusted slightly, so as to make the electrodes 2 in close contact with the tube wall and improve the wall attaching state of the electrodes 2. According to the radiofrequency ablation catheter, due to the fact that the supporting, wall-attaching adjustment wire 6 is arranged inside the electrode frame, when the supporting, wall-attaching adjustment wire 6 is pulled again after the flexible segment 61 of the supporting, wall-attaching adjustment wire 6 overlaps with the outer tube of the electrode frame, the motion range of the supporting, wall-attaching adjustment wire 6 is small, and therefore only fine adjustment of the shape of the electrode frame can be achieved. During selection of radiofrequency ablation catheters, a radiofrequency ablation catheter with corrugated segment diameter larger than or close to target lumen diameter is suggested, so that when an electrode frame automatically expands in a target lumen to recover to be corrugated, the electrode frame can be tightly attached to the wall under the action of the vessel wall. The radiofrequency ablation catheter has a good wall attaching effect for target lumens with diameter smaller than or equal to the initial diameter of the corrugated segment.

In addition, the present invention further provides a radiofrequency ablation catheter provided with the supporting, wall-attaching adjustment wire 6 and a wall-attaching adjustment wire 8 at the same time, wherein the rear segment of the wall-attaching adjustment wire 8 is slidably provided within one lumen of the connecting catheter 10, and the rear extremity of the wall-attaching adjustment wire 8 penetrates into the control handle 20 and is then connected to the control element arranged on the control handle 20, or the rear extremity of the wall-attaching adjustment wire 8 passes through the control handle 20 and is then connected to the control element arranged externally; the front segment of the wall-attaching adjustment wire 8 protrudes to the outside of the electrode frame and either runs through one or more holes provided on the corrugations or runs around the multiple corrugations, and then the front extremity returns to the interior of the electrode frame to be fixed. By pulling back the wall-attaching adjustment wire 8, the diameter of the corrugated segment can be changed substantially so as to adapt to blood vessels with different diameters, in this case, the initial diameter of the corrugated shape of the electrode frame can be smaller than the diameter of the target lumen. Please refer to the fifth embodiment to the seventh embodiment for the specific structure of the radiofrequency ablation catheter provided with the supporting, wall-attaching adjustment wire 6 and the wall-attaching adjustment wire 8 at the same time. The wall-attaching adjustment wire 8 can be an additionally arranged filament, and the wall-attaching adjustment wire 8 can also be a filament branch obtained through outward branching of the supporting, wall-attaching adjustment wire 6. The arrangement of the wall-attaching adjustment wire 8 will be described in detail hereinafter with reference to specific embodiments, no description here.

The specific structure of the supporting, wall-attaching adjustment wire 6 which can be used in the corrugated radiofrequency ablation catheter provided by the present invention will be explained next with reference to FIG. 6 to FIG. 8.

The supporting, wall-attaching adjustment wire 6 is provided with the flexible segment 61 (in proximity to the head end) away from the control handle 20 and the rigid segment 62 (in proximity to the tail end) in proximity to the control handle 20, and the supporting, wall-attaching adjustment wire 6 can be made of a polymer material or a metal material, and can be a wire or a tube. As shown in FIG. 6, the flexible segment 61 of the supporting, wall-attaching adjustment wire 6 can be made into a spiral shape with a filament, and the rigid segment 62 can be made of a wire with a relatively large diameter or high rigidity. As shown in FIG. 7, the requirement for the flexibility and the rigidity of the flexible segment 61 and the rigid segment 62 of the supporting, wall-attaching adjustment wire 6 can be met by means of the same kind of wire with different diameters. The supporting, wall-attaching adjustment wire 6 can also be assembled with materials with different rigidities, so as to meet the requirement for a flexible front segment and a rigid rear segment. Besides, as shown in FIG. 8, the supporting, wall-attaching adjustment wire 6 can also be made of one piece of rigid material, and the front segment of the material is provided with grooves and/or holes and the like so as to become the flexible segment 61. Or the supporting, wall-attaching adjustment wire 6 is made of one piece of flexible material, and the rear segment of the material is provided with an outer sleeve so as to become the rigid segment 62. Of course, the flexible segment and the rigid segment of the supporting, wall-attaching adjustment wire 6 can also be realized in other ways. For example, the flexible segment 61 can be made of a hose or spring.

Figure 7:
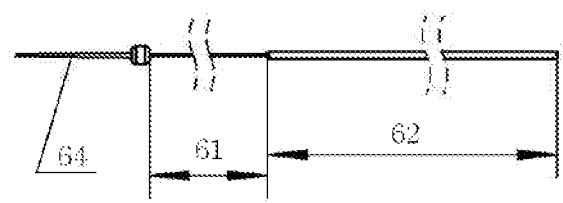
FIG. 7 is a structure diagram of a second supporting, wall-attaching adjustment wire of the present invention.
Figure 8:
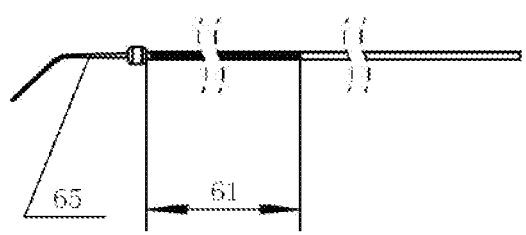
FIG. 8 is a structure diagram of a third supporting, wall-attaching adjustment wire of the present invention.

As shown in FIG. 6 to FIG. 8, a developing head 63 can be arranged at the head end of the supporting, wall-attaching adjustment wire 6 to be used for real-time imaging of the interior of the target lumen. Meanwhile, a soft guide wire can also be arranged at the front extremity of the supporting, wall-attaching adjustment wire 6, the soft guide wire can be a straight-bead soft guide wire 64 as shown in FIG. 7, and can also be a bent-head soft guide wire 65 as shown in FIG. 8, in this way, the radiofrequency ablation catheter can directly enter blood vessels without a catheter guide tube/sheath, and surgical procedures are simplified.

Second to Fourth Embodiments

In the second embodiment as shown in FIG. 9A and FIG. 9B, every two arc waves are located in the same plane, so that the profile projections of the multiple corrugations are in a radial shape as shown in FIG. 9B. The multiple electrodes 2 can be distributed on the corrugations respectively, and preferably, the electrodes 2 are provided at the crests/trough of the corrugations. It can be learnt from the side view as shown in FIG. 9B that in the present embodiment, the profile projections of the corrugations in the corrugated electrode frame are distributed in a crossing mode, and the multiple electrodes 2 are arranged at the crest positions (also called troughs) respectively. When the corrugations cross each other at the same angle, the profile projections, on the electrode frame, of the multiple electrodes 2 can be evenly distributed in the circumferential direction, in other words, the profile projections are distributed on the outer periphery of the target lumen into an approximate circle. Of course, when the crossing angles of the corrugations are different, the profile projections, on the electrode frame, of the multiple electrodes 2 can be distributed unevenly in the circumferential direction. Besides, when the electrode frame is long, the multiple corrugations, in the length direction, of the electrode frame can be repeated regularly or randomly, so that the profile projections, on the electrode frame, of the multiple electrodes 2 can overlap.

In the third embodiment as shown in FIG. 10A and FIG. 10B, the corrugated electrode frame is composed of multiple arc waves, but the multiple corrugations are located in different planes. The multiple electrodes are located at the crests of the arc waves respectively, so that the profile projections of the multiple electrodes can be distributed in the circumferential direction of the target lumen. In this case, after ablation is finished once, the catheter can be directly moved to conduct ablation on other portions of the target lumen.

In the fourth embodiment as shown in FIG. 11A and FIG. 11B, the multiple corrugations of the corrugated electrode frame are all located in different planes, moreover the multiple corrugations are distributed into an approximate spiral shape, the multiple electrodes are located at the crests of the corrugations respectively, and therefore the multiple electrodes can also be distributed in the circumferential direction of the target lumen. In the present embodiment, the multiple corrugations can be distributed into one or more circles of spirals.

It can be learnt from the above four embodiments that the multiple corrugations in the corrugated electrode frame can be in the shape of a triangular wave composed of several straight line segments, an arc wave (see FIG. 9A and FIG. 10A) or sine wave (see FIG. 1A) composed of several arc segments, a trapezoidal wave composed of straight lines and curves, or any other corrugations not shown in the figures. The multiple corrugations can be distributed in the same plane, can also be distributed in different planes, and can even be distributed into an approximate spiral shape in an encircling mode, so that the electrodes can be distributed in the circumferential direction. Compared with the situation that the multiple corrugations are distributed in the same plane, when the multiple corrugations are distributed in different planes, the corrugated electrode frame can be attached to the wall in any direction in the target lumen during actual ablation surgery. Besides, in the above-mentioned embodiments as shown in the figures, on the same electrode frame, the multiple corrugations forming the corrugated shape are in the same shape. Of course, the multiple corrugations forming the corrugated shape can have different shapes, and sizes, and the corrugations can be different in form, spacing, crest position, trough position and the like. When the corrugated electrode frame consists of corrugations in different sizes, the wall-attaching states of local electrodes can be adjusted by adjusting the sizes of the corrugations in a local area, and at the same time, the forms of other areas may not be adjusted. Wall-attaching adjustment of the corrugated electrode frame consisting of different corrugations can be achieved by pulling the supporting, wall-attaching adjustment wire 6 to enable different areas of the supporting, wall-attaching adjustment wire 6 to overlap with the electrode frame, and can also be achieved by pulling the wall-attaching adjustment wire 8. Please see the eighth embodiment for the structure of the wall-adjustment adjustment wire 8 composed of multiple filaments and the wall-attaching adjustment way.

In conclusion, by arranging the supporting, wall-attaching adjustment wire provided with the flexible segment and the rigid segment in the corrugated radiofrequency ablation catheter, diameter change of the electrode frame can be achieved without the aid of a catheter guide tube/sheath so that the electrode frame can enter the sheath/target lumen easily, and part of or all of the electrode frame can be selectively recovered to be corrugated after entering the target lumen.

Fifth Embodiment

It can be learnt from FIG. 12A to FIG. 17 that in the radiofrequency ablation catheter provided in the present embodiment, a lumen used for accommodating the wall-attaching adjustment wire 8 is further provided in the outer tube 1 of the electrode frame and the connecting catheter 10, the rear segment of the wall-attaching adjustment wire 8 is slidably provided within one lumen of the connecting catheter, the rear extremity 80 of the wall-attaching adjustment wire 8 is connected to the control element 23 provided outside the control handle 20 (see FIG. 17), and the wall-attaching adjustment wire 8 can slide forward and backward in the lumen of the connecting catheter. The lumen for accommodating the wall-attaching adjustment wire 8 can be the central lumen or one of the multiple eccentric lumens distributed on the periphery of the central lumen. As shown in FIG. 12A, the front segment of the wall-attaching adjustment wire 8 runs through a hole in proximity to the rear extremity of the electrode frame, protrudes to the outside the electrode frame and runs through multiple holes provided on different corrugations, and finally the front extremity of the wall-attaching adjustment wire 8 runs through a hole in proximity to the front extremity of the electrode frame and returns to the interior of the electrode frame to be fixed. The wall-attaching adjustment wire 8 can slide in the holes provided on different corrugations.

The front extremity of the wall-attaching adjustment wire 8 can be fixed at different positions, and the front extremity of the wall-attaching adjustment wire 8 can be fixed to the front extremity of the electrode frame, to the front extremity of the supporting, wall-attaching adjustment wire 6, or to the shaping wire 7, or the front extremity of the wall-attaching adjustment wire 8 runs the corresponding lumens in the electrode frame 2 and the connecting catheter to be fixed to the control element 23 or a housing of the control handle 20 together with the rear extremity 80 of the wall-attaching adjustment wire 8.

Figure 15:
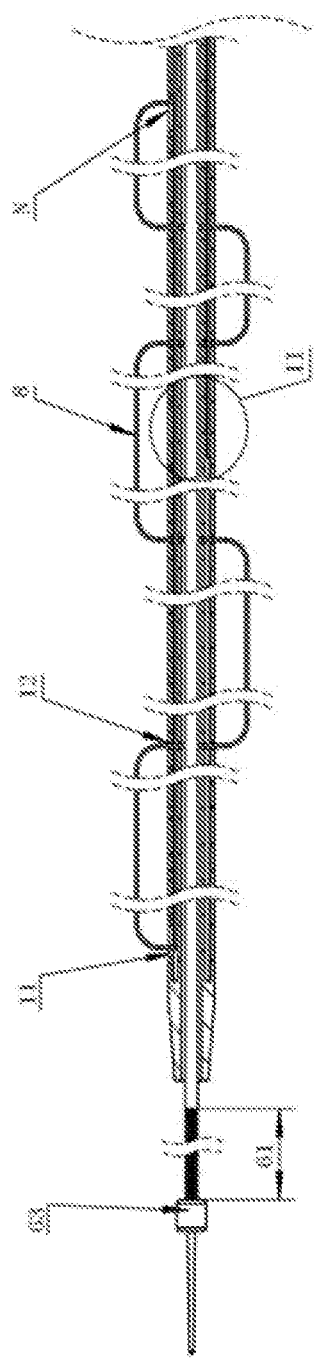
FIG. 15 is an F-F cross section view of the corrugated radiofrequency ablation catheter in the fifth embodiment when a rigid segment of a supporting, wall-attaching adjustment wire overlaps with the electrode frame.
Figure 16:
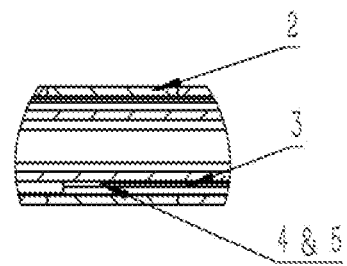
FIG. 16 is a local enlarged view of a portion II of the corrugated radiofrequency ablation catheter shown in FIG. 15.
Figure 17:
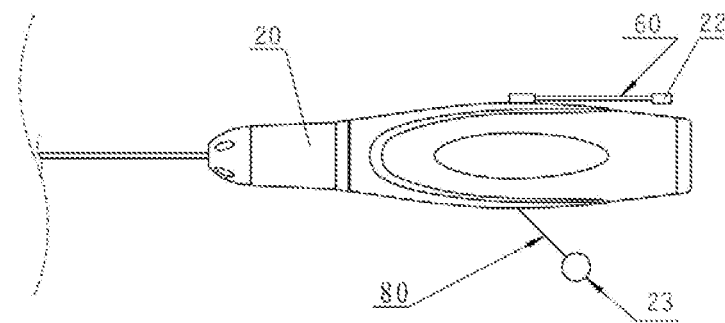
FIG. 17 is a structure diagram of a control handle of the radiofrequency ablation catheter shown in the fifth embodiment.

Specifically, as shown in FIG. 15, after running through the hole 11 in proximity to the front extremity of the electrode frame and returning to the interior of the electrode frame 2, the front extremity of the wall-attaching adjustment wire 8 runs through the lumens in the electrode frame and the connecting catheter, returns to the rear extremity of the connecting catheter together with the rear extremity of the wall-attaching adjustment wire 8, and is fixed to the housing of the control handle 20 or the button control element 22. In other words, the front extremity and the rear extremity of the wall-attaching adjustment wire 8 can be fixed to the same control element 23 as shown in FIG. 17, or either the front extremity or the rear extremity of the wall-attaching adjustment wire 8 is fixed to the housing of the control handle 20, and the other one is fixed to the control element 23. By pulling the control element 23, the wall-attaching adjustment wire 8 is driven to move backwards, and the diameter of the electrode frame can be changed significantly.

Of course, the front extremity of the wall-attaching adjustment wire 8 can also be simply fixed to the front extremity of the electrode frame, or fixed to the front extremity of the supporting, wall-attaching adjustment wire 6 or a certain portion, located in the electrode frame, of the supporting, wall-attaching adjustment wire 6, or fixed to a certain position on the shaping wire 7, or the front extremity of the wall-attaching adjustment wire 8 is fixed in the lumen of the electrode frame, as long as the front extremity of the wall-attaching adjustment wire 8 is fixed. In this way, when the wall-attaching adjustment wire 8 is pulled back, contraction distortion of the electrode frame can be caused under the action of the wall-attaching adjustment wire 8, the diameters of the corrugations of the electrode frame are increased, and the axial distance between the multiple corrugations becomes smaller. When the front extremity of the wall-attaching adjustment wire 8 is fixed to the supporting, wall-attaching adjustment wire 6 or the shaping wire 7, the wall-attaching adjustment wire 8 and the supporting, wall-attaching adjustment wire 6/shaping wire 7 can be made of the same material, and in this case, the wall-attaching adjustment wire 8 can be interpreted as a filament obtained through backward branching of the supporting, wall-attaching adjustment wire 6/shaping wire 7.

Figure 18:
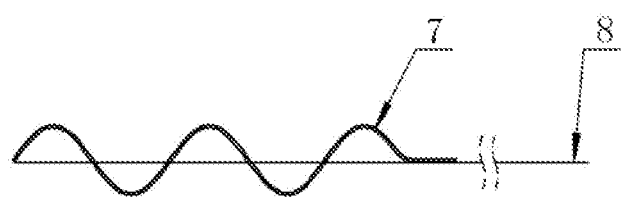
FIG. 18 is a structure diagram of a wall-attaching adjustment wire fixed to a shaping wire in the fifth embodiment.

For example, as shown in FIG. 18, the front extremity of the wall-attaching adjustment wire 8 and the front extremity of the shaping wire 7 are fixed together, in this case, the shaping wire 7 and the wall-attaching adjustment wire 8 can be made of the same kind of filament, the wall-attaching adjustment wire 8 and the shaping wire 7 are two filament branches obtained through backward branching of the front extremity of the filament respectively, wherein the branch corresponding to the shaping wire 7 is fixed in a certain lumen of the electrode frame, and the rear segment of the branch corresponding to the wall-attaching adjustment wire 8 can slide in the corresponding lumen of the electrode frame and/or the connecting catheter. When the wall-attaching adjustment wire 8 and the shaping wire 7 are made of different materials (for example, the shaping wire 7 is made of tubing and the wall-attaching adjustment wire 8 is made of a filament), the front extremity/front segment of the wall-attaching adjustment wire 8 and the shaping wire 7 can be assembled together through welding, riveting, bonding or other techniques.

Figure 19A:
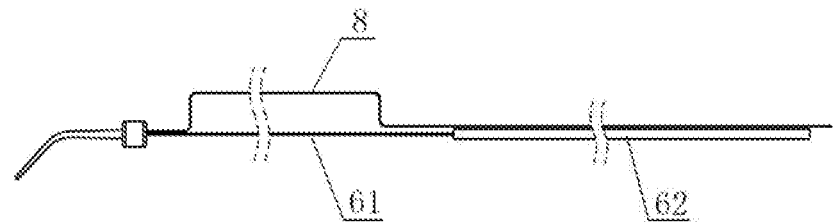
FIG. 19A, FIG. 19B and FIG. 19C are structure diagrams of three supporting, wall-attaching adjustment wires with branches respectively in the fifth embodiment.
Figure 19B:
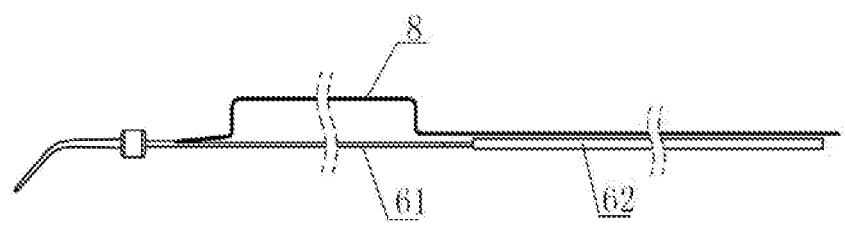
Figure 19C:
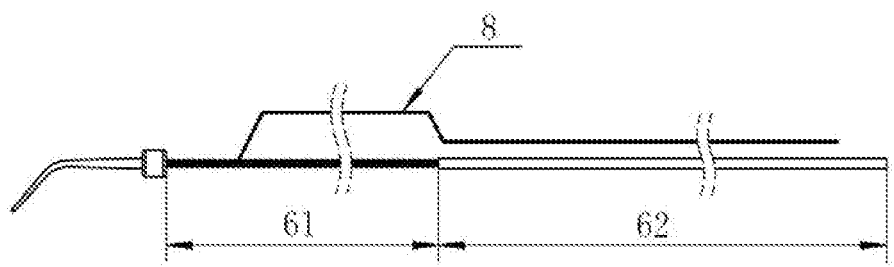

In the three structures as shown in FIG. 19A to FIG. 19C, the front extremity of the wall-attaching adjustment wire 8 and the supporting, wall-attaching adjustment wire 6 are fixed together, and the front extremity of the wall-attaching adjustment wire 8 can be fixed to the front extremity of the supporting, wall-attaching adjustment wire 6, or to the flexible segment 61 as shown in FIG. 19B and FIG. 19C. The supporting, wall-attaching adjustment wire 6 and the wall-attaching adjustment wire 8 can be made of the same kind of filament, the wall-attaching adjustment wire 8 and the supporting, wall-attaching adjustment wire 6 are two filament branches obtained through backward branching of the front extremity of the filament, the branch corresponding to the supporting, wall-attaching adjustment wire 6 and the branch corresponding to the wall-attaching adjustment wire 8 can be arranged in different lumens of the electrode frame respectively, and the rear segment of the branch corresponding to the wall-attaching adjustment wire 8 protrudes to the outside the electrode frame and runs around the electrode frame, then returns to the interior of the connecting catheter, runs through the lumen in the connecting catheter, and returns to the rear extremity of the connecting catheter to be fixed to the corresponding control element 23. The branch corresponding to the supporting, wall-attaching adjustment wire 6 and the branch corresponding to the wall-attaching adjustment wire 8 can also be arranged in the same lumen of the electrode frame. When the wall-attaching adjustment wire 8 and the supporting, wall-attaching adjustment wire 6 are made of different materials, for example, as shown in FIG. 19C, when the flexible segment 61 of the supporting, wall-attaching adjustment wire 6 is made of a spring and the wall-attaching adjustment wire 8 is made of a filament, the front extremity font segment of the wall-attaching adjustment wire 8 and the supporting, wall-attaching adjustment wire 6 can be assembled together through welding, riveting, bonding or other techniques.

It can be seen from FIG. 17 that in the present embodiment, the button control element 22 is arranged on the control handle 20, a control element 23 used for being connected with the wall-attaching adjustment wire 8 is arranged outside the control handle 20, and the tail end 60 of the supporting, wall-attaching adjustment wire 6 protrudes to the outside of the connecting catheter, then enters the control handle 20, and is fixed to the button control element 22; the tail end 80 of the wall-attaching adjustment wire 8 enters the control handle 20 too after protruding to the outside of the connecting catheter, and is then fixed to the externally arranged control element 23 after running through the control handle 20. Of course, the button control element 22 connected with the supporting, wall-attaching adjustment wire 6 can also be provided outside the control handle 20 in an externally arranged way, and the rear extremity of the supporting, wall-attaching adjustment wire 6 passes through the control handle 20 and then is connected to the externally arranged button control element 22. Similarly, the control element 23 can also be arranged on the control handle 20, and the wall-attaching adjustment wire 8 penetrates into the control handle 20 and is then directly connected with the control element 23.

FIG. 12A to FIG. 13B show the use state views of the corrugated radiofrequency ablation catheter provided with the wall-attaching adjustment wire 8 after the corrugated radiofrequency ablation catheter enters target lumens with different diameters. Suppose the corrugated electrode frame has an initial diameter of ΦB and a corrugated segment length of A. By loosening the wall-attaching adjustment wire 8, the wall-attaching adjustment wire 8 becomes loose, at the moment; the length of the corrugated segment at the front extremity of the catheter can be increased by moving the supporting, wall-attaching adjustment wire 6 forward, so that the corrugated segment is approximately straight and can enter the target lumen. As shown in FIG. 12A, when the corrugated electrode frame enters a thin blood vessel from the sheath (suppose the diameter of the target lumen ΦC is smaller than or equal to the initial diameter of the corrugations ΦB), the supporting, wall-attaching adjustment wire 6 is pulled backward so that the flexible segment 61 enters the interior of the electrode frame, the corrugations of the electrode frame automatically expand to have a diameter close to the diameter of the target lumen ΦC, the multiple electrodes 2 make contact with the wall of the catheter under the natural expansion of the electrode frame, at the moment, the length of the corrugated segment of the electrode frame is increased to be (A-1), and the wall-attaching state of the electrodes 2 can be improved by tensioning the wall-attaching adjustment wire 8. As shown in FIG. 13A, when the corrugated electrode frame enters a thick blood vessel from the sheath (suppose the diameter of the target lumen is larger than or equal to the initial diameter of the corrugations ΦB), the electrodes 2 can not be well attached to the wall after the electrode frame expands naturally, at the moment, by pulling back the wall-attaching adjustment wire 8, the diameters of the corrugations of the electrode frame can be increased to be equal to or slightly larger than the diameter of the target lumen ΦD (see FIG. 3B), and the multiple electrodes 2 make close contact with, the wall of the catheter under the action of the wall-attaching adjustment wire 8. At the moment, the length of the corrugated segment of the electrode frame is shortened to be (A-2), and the axial distance between the multiple electrodes distributed on the electrode frame becomes smaller. After radiofrequency ends, by loosening the wall-attaching adjustment wire 8, the electrode frame becomes loose, then the supporting, wall-attaching adjustment wire 6 is moved forward to enable the rigid segment 62 to enter the interior of the electrode frame, and the electrode frame tends to be linear and can enter the sheath easily, so that the radiofrequency ablation catheter can be rotated or moved in the target lumen, or moved out of the target lumen.

Sixth Embodiment

Figure 20:
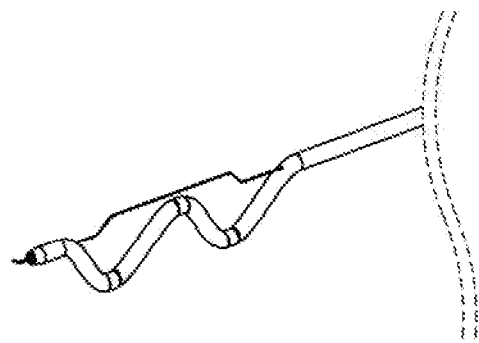
FIG. 20 is a three-dimensional structure diagram of a first corrugated radiofrequency ablation catheter in the sixth embodiment.
Figure 21:
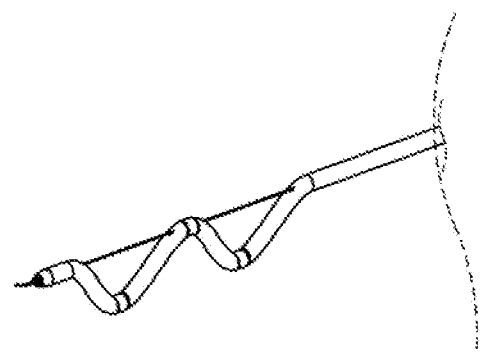
FIG. 21 is a three-dimensional structure diagram of a second corrugated radiofrequency ablation catheter in the sixth embodiment.

FIG. 20 and FIG. 21 are two structure diagrams of the radiofrequency ablation catheter in the sixth embodiment. In the present embodiment, the wall-attaching adjustment wire 8 is eccentrically arranged on the corrugated electrode frame, and the wall-attaching adjustment wire 8 can be located at the highest point of the electrode frame and can also be located at any position between the center and the vertex of the electrode frame.

In the structure as shown in FIG. 20, the wall-attaching adjustment wire 8 is eccentrically arranged on the corrugated electrode frame, and the front segment of the wall-attaching adjustment wire 6 penetrates out of the hole in proximity to the rear end of the electrode frame, runs around the multiple corrugations, runs through the hole in proximity to the front extremity of the electrode frame and then enters the front extremity of the electrode frame to be fixed.

In the structure as shown in FIG. 21, the wall-attaching adjustment wire 8 is eccentrically arranged on the corrugated electrode frame, and the front segment of the wall-attaching adjustment wire 8 penetrates out of the hole in proximity to the rear extremity of the electrode frame, runs through the holes provided on the corrugations, runs through the hole in proximity to the front extremity of the electrode frame and then enters the front extremity of the electrode frame to be fixed.

In the radiofrequency ablation catheter as shown in FIG. 21, the electrode frame has two corrugations, the wall-attaching adjustment wire 8 is eccentrically arranged, and the wall-attaching adjustment wire 8 can be composed of one filament or two filaments.

Figure 22:
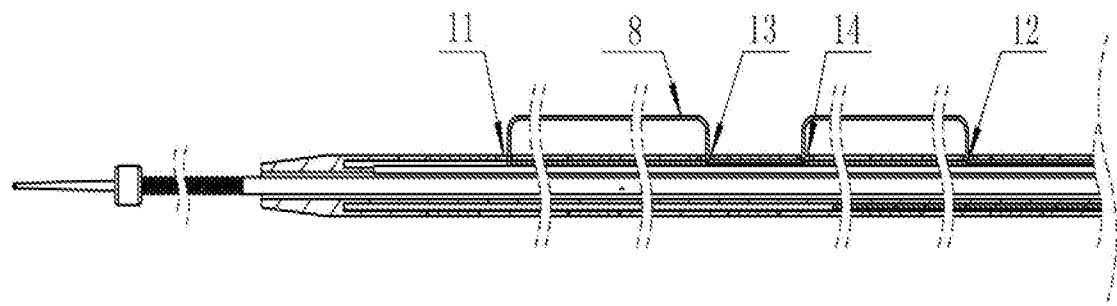
FIG. 22 is an internal structure diagram of the corrugated radiofrequency ablation catheter shown in FIG. 21.

In the structure as shown in FIG. 22, the wall-attaching adjustment wire 8 is composed of one filament, the rear segment of the wall-attaching adjustment wire 8 runs through the lumen in the connecting catheter and returns to the interior of the control handle 20, and the rear extremity of the wall-attaching adjustment wire 8 is fixed to the control element provided on the control handle 20 or the control element arranged externally; the middle segment of the wall-attaching adjustment wire 8 penetrates out of the hole 12 in proximity to the rear extremity of the electrode frame, and then two points are fixed to the interior of a hole 13 and a hole 14 provided at the crest at the middle position between two corrugations respectively; then the front extremity of the wall-attaching adjustment wire 8 runs through the hole 11 in proximity to the front extremity of the electrode frame, enters the interior of the electrode frame, runs through the lumen in the electrode frame and the connecting catheter, returns to the rear extremity of the connecting catheter, and is fixed to the same control element with the rear extremity or to different control elements with the rear extremity. In such a structure, both the front extremity and the rear extremity of the wall-attaching adjustment wire 8 pass through the lumen inside the connecting catheter, the front extremity and the rear extremity of the wall-attaching adjustment wire 8 are fixed to the corresponding control elements respectively, and both of the two corresponding control elements can be arranged on the control handle 20 or outside the control handle 20, or one control element is arranged on the control handle 20, and the other control element is arranged outside the control handle 20. The front segment and the rear segment of the wall-attaching adjustment wire 8 are controlled through the two corresponding control elements respectively, and the contraction degrees of two corrugations can be separately adjusted. Furthermore, the front extremity and the rear extremity of the wall-attaching adjustment wire 8 can be fixed to the same control element, so that the contraction degree of two corrugations can be controlled by one control element at the same time.

Figure 23:
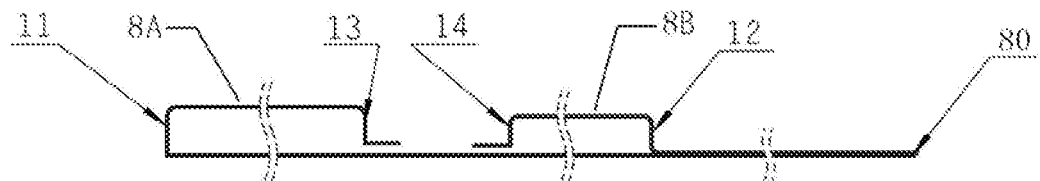
FIG. 23 is a structure diagram of a second wall-attaching adjustment wire in the corrugated radiofrequency ablation catheter shown in FIG. 21.
Figure 24:
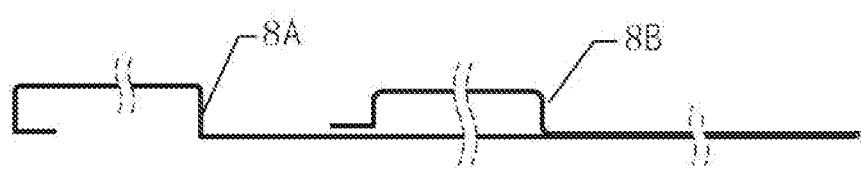
FIG. 24 is a structure diagram of a third wall-attaching adjustment wire in the corrugated radiofrequency ablation catheter shown in FIG. 21.

As shown in FIG. 23 and FIG. 24, in the structure as shown in FIG. 21, the wall-attaching adjustment wire 8 can also be composed of two filaments 8A and 8B used for adjusting two corrugations respectively, the front extremity of each filament is fixed to one end of the corresponding corrugation, and the other extremity of each filament runs around the corresponding corrugation, returns to the interior of the electrode frame from the other end of the corrugation, runs through the lumen in the electrode frame and the connecting catheter, returns to the control handle, and is fixed to the corresponding control element arranged on the control handle or arranged externally.

In FIG. 23, the front extremity of the filament 8A is fixed in the hole 13 provided between the two corrugations, and the rear extremity of the filament 8A runs around the corrugation on the left side, runs through the hole 11 in proximity to the front extremity of the electrode frame, returns to the interior of the electrode frame, runs through the lumen in the electrode frame and the connecting catheter, returns to the control handle, and is fixed to the corresponding control element; the front extremity of the filament 8B is fixed in the other hole 14 provided between the two corrugations, and the rear extremity of the filament 8B runs around the corrugation on the right side, runs through the hole 12 in proximity to the rear extremity of the electrode frame, returns to the interior of the electrode frame, runs through the lumen in the electrode frame and the connecting catheter, returns to the control handle, and is fixed to the corresponding control element. In FIG. 24, the filament 8B is arranged in the same way as FIG. 23, the front extremity of the filament 8A is fixed in the hole 11 in proximity to the front extremity of the electrode frame, and the rear extremity of the filament 8A runs around the corrugation on the left side, runs through the hole 13 provided between the two corrugations, returns to the interior of the electrode frame, runs through the lumen in the electrode frame and the connecting catheter, returns to the control handle, and is fixed to the corresponding control element. The two corresponding control elements fixed to the filament 8A and the filament 8B respectively can be arranged on the control handle 20 or outside the control handle 20. The wall-attaching adjustment filaments 8A and 8B are used for controlling the contraction degrees of the two corrugations respectively. The wall-attaching adjustment filaments 8A and 8B are controlled through the two corresponding control elements respectively, and the contraction degrees of two corrugations can be separately adjusted. Furthermore, the corresponding control elements of the filament 8A and the filament 8B can be the same control element.

Seventh Embodiment

Figure 25:
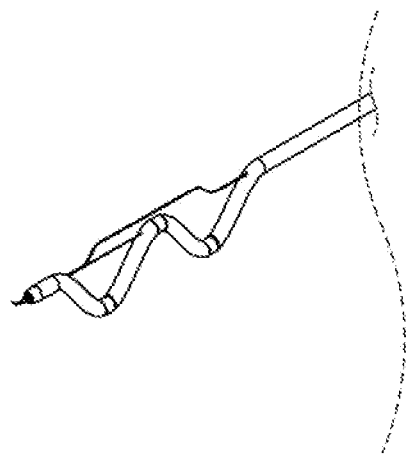
FIG. 25 is a three-dimensional structure diagram of a corrugated radiofrequency ablation catheter in the seventh embodiment.
Figure 26:
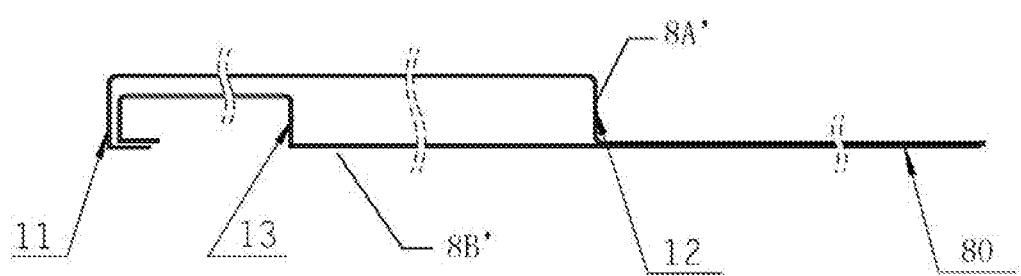
FIG. 26 is a structure diagram of a wall-attaching adjustment wire in the corrugated radiofrequency ablation catheter shown in FIG. 25.

In the seventh embodiment shown in FIG. 25 and FIG. 26, the wall-attaching adjustment wire 8 is composed of two filaments 8A' and 8B' used for adjusting one corrugation and one segment of corrugations (namely a corrugated segment) respectively, the front extremity of each filament is fixed to one end of the corresponding corrugation/corrugated segment, and the other extremity of each filament runs around the corresponding corrugation/corrugated segment and returns to the interior of the electrode frame from the other end of the corrugation/corrugated segment, runs through the lumen in the electrode frame and the connecting catheter, returns to the control handle, and is fixed to the corresponding control elements. As shown in FIG. 26, the front extremity of the filament 8A' and the front extremity of the filament 8B' are both fixed in the hole 11 in proximity to the front extremity of the electrode frame, and the rear extremities 80 of the two filaments run through the hole 13 provided between two corrugations and the hole 12 in proximity to the rear extremity of the electrode frame, return to the interior of the electrode frame respectively, and are finally fixed to the corresponding control elements. The filament 8A' is used for controlling the contraction degree of the single corrugation in proximity to the front extremity of the electrode frame, the filament 8B' is used for controlling the whole corrugated segment, in the present embodiment as shown in the figure, the whole corrugated segment comprises two corrugations, that is to say, the filament 8B' is used for controlling the contraction degree of the two corrugations. The corrugated segment adjusted by the filament 8B' comprises the single corrugation adjusted by the filament 8A'. In the present embodiment, the corresponding control elements connected with the rear extremities of the two filaments respectively can also be one control element.

It can be learnt from the sixth embodiment and the seventh embodiment that when the electrode frame has two or more corrugations, the wall-attaching adjustment wire 8 can be composed of two or more filaments, the multiple filaments are used for adjusting one corrugation or one segment of corrugations on the electrode frame respectively, wherein one segment of corrugations comprises two or more corrugations, the front extremity of each filament is fixed to one end of the corresponding corrugation/corrugated segment, and the other extremity of each filament runs around the corresponding corrugation/corrugated segment, returns to the interior of the electrode frame from the other end of the corrugation/corrugated segment, and is fixed to the corresponding control elements through the lumen in the electrode frame and the connecting catheter. When one filament is used for adjusting a single corrugation, the front extremity of the filament is fixed to one end of the corrugation, and the rear extremity of the filament runs through the hole formed in the other end of the corrugation and penetrates into the electrode frame; when one filament is used for adjusting a certain segment of corrugations, the front extremity of the filament is fixed to one end of the segment of corrugations, and the rear extremity of the filament runs through the hole formed in the other end of the segment of corrugations and penetrates into the electrode frame. The multiple segments of corrugations controlled by the multiple filaments respectively can overlap. In the structure shown in FIG. 23 and FIG. 24, the wall-attaching adjustment wire has two filaments, and the two filaments are used for adjusting two corrugations on the electrode frame respectively; while in the structure of the seventh embodiment shown in FIG. 25 and FIG. 26, the wall-attaching adjustment wire 8 has two filaments, and the two filaments are used for controlling one corrugation and one segment of corrugations on the electrode frame respectively.

When multiple control elements are adopted to control different corrugated segments of the electrode frame respectively, after the radiofrequency ablation catheter enters a target position, the corresponding corrugated segments of the electrode frame can be expanded in a segmented mode as needed, in other words, only the diameters of the corrugated segments requiring radiofrequency are changed, in this way, the diameters of different corrugated segments of the electrode frame can be adjusted more flexibly, and the wall-attaching adjustment difficulty of the radiofrequency ablation catheter is reduced.

Furthermore, the rear extremities of the multiple filaments can also be fixed to one control element, so that one control element can control all the filaments.

Eighth Embodiment

Figure 27:
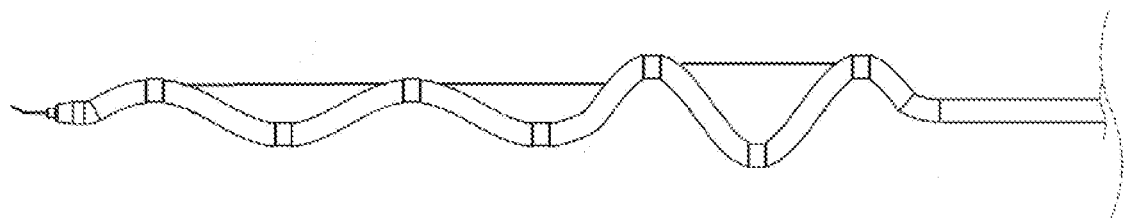
FIG. 27 is a three-dimensional structure diagram of a corrugated radiofrequency ablation catheter in the eighth embodiment.

As shown in FIG. 27, the electrode frame of the radiofrequency ablation catheter provided in the present embodiment is composed of multiple corrugations in different sizes. Every corrugation can have its own size, or part of the corrugations can have one size and others have a different size.

The multiple corrugations can also be arranged from the front extremity to the rear extremity of the electrode frame in a size increasing mode. By pulling the supporting, wall-attaching adjustment wire 6, part of the flexible segment 61 can be controlled to overlap with the front segment of the electrode frame and part of the rigid segment 62 can be controlled to overlap with the rear segment of the electrode frame, in this case, the front segment of the electrode frame recovers to be corrugated and the rear segment of the electrode frame still tends to be linear, so that the electrode frame can be attached to the wall in blood vessels with different diameters. For example, when the diameter of a target ablation position is small, part of the flexible segment 61 can be made to overlap with the front segment of the electrode frame and part of the rigid segment 62 can be made to overlap with the rear segment of the electrode frame by pulling the supporting, wall-attaching adjustment wire 6, a good wall-attaching condition of the electrodes can be achieved by pulling the wall-attaching adjustment wire 8, and then the small-diameter target lumen can be ablated. When the diameter of a target ablation position is large, the flexible segment 61 can be made to overlap with the whole electrode frame and the rigid segment 62 retreats into the connecting catheter by pulling the supporting, wall-attaching adjustment wire 6, in this case, the wall-attaching state of the electrodes can be improved by pulling the wall-attaching adjustment wire 8, and then the large-diameter target lumen can be ablated.

When the wall-attaching adjustment wire 8 composed of multiple filaments is arranged in the radiofrequency ablation catheter, the different filaments are used for controlling different parts of the electrode frame respectively, and the corrugation size of a corresponding area of a corrugated segment can be changed by pulling the different filaments, so that local wall attaching of the electrode frame can be achieved. Please refer to the sixth embodiment and the seventh embodiment for the specific arrangement mode of the wall-attaching adjustment wire 8 composed of multiple filaments, and the descriptions thereof are omitted herein.

When the multiple corrugations are provided from the front extremity to the rear extremity of the electrode frame in a size increasing mode, the radiofrequency ablation catheter using the electrode frame can also be suitable for the situation that the diameter of a target lumen becomes smaller gradually. For example, the radiofrequency ablation catheter can enter a small branch blood vessel with a small diameter from a blood vessel with a large diameter for ablation. In this case, the multiple filaments corresponding to small-diameter corrugated segments can be controlled to allow the small-diameter corrugated segments to be well attached to the wall, so that the small branch blood vessel can be ablated by means of the small-diameter corrugated segments; or, large-diameter corrugated segments and the small-diameter corrugated segments can be attached to the wall at the same time by controlling the multiple filaments, so that the large blood vessel and the small blood vessel can be ablated at the same time or in sequence.

Similarly, the multiple corrugations constituting the electrode frame can be arranged from the front extremity to the rear extremity of the electrode frame in a size reducing mode. As is the case with the situation when the multiple corrugations are arranged from the front extremity to the rear extremity of the electrode frame in a size reducing mode, by controlling different areas of the supporting, wall-attaching adjustment wire 6 to overlap with the electrode frame, the diameter of the corrugated segment of the electrode frame can be changed, so that ablation of the radiofrequency ablation catheter in blood vessels with different diameters can be achieved. When the wall-attaching adjustment wire 8 composed of multiple filaments is arranged in the radiofrequency ablation catheter, the different filaments are used for controlling different parts of the electrode frame respectively, and the corrugation size of a corresponding area of a corrugated segment can be changed by pulling different filaments, so that local wall attaching of the electrode frame can be achieved. When the multiple corrugations are provided from the front extremity to the rear extremity of the electrode frame in a size reducing mode, the radiofrequency ablation catheter using the electrode frame is suitable for the situation that the diameter of a target lumen becomes larger gradually. For example, the radiofrequency ablation catheter is suitable for sympathetic denervation ablation of the pelvis region via the urethral system, the catheter runs through the urethra, enters the bladder, enters the fallopian tube and reaches the pelvis region, at the moment, the large-diameter corrugated segments can be well attached to the wall of the pelvis region and the small-diameter corrugated segments can be well attached to the wall of the fallopian tube by adjusting the wall-attaching adjustment wire, so that sympathetic nerves in proximity to the fallopian tube and the pelvis region can be ablated at the same time.

In conclusion, the supporting, wall-attaching adjustment wire provided with the flexible segment and the rigid segment is arranged in the corrugated radiofrequency ablation catheter, by moving the wall-attaching adjustment wire forward, the rigid segment can overlap with the electrode frame, so that the form of the electrode frame is changed, the electrode frame tends to be linear, and the radiofrequency ablation catheter can enter the sheath or the target lumen easily; furthermore, after the radiofrequency ablation catheter enters the target lumen, by pulling the wall-attaching adjustment wire backward, the flexible segment overlaps with the electrode frame, so that the electrode frame recovers to be corrugated and wall attaching is achieved. To realize a better wall attaching effect and adapt to blood vessels with different diameters, the wall-attaching adjustment wire can also be arranged in the corrugated radiofrequency ablation catheter, and by pulling the wall-attaching adjustment wire backward, the corrugation diameter of the electrode frame can be changed. Furthermore, the wall-attaching adjustment wire can be of a multi filament structure, so as to control different corrugated segments of the radiofrequency ablation catheter, and reduce the difficulty of diameter adjustment.

In actual clinical treatment, the radiofrequency ablation catheter and a radiofrequency ablation apparatus provided by the present invention can be applied to different positions and blood vessels or tracheae with different diameters for neuroablation. For example, the radiofrequency ablation catheter and the radiofrequency ablation apparatus can be applied to neuroablation in the renal artery to treat resistant hypertension, neuroablation in the arteria coeliaca to treat diabetes, trachea/bronchus vagus nerve branch ablation to treat asthma, and duodenum vagus nerve branch ablation to treat duodenal ulcers; besides, the radiofrequency ablation catheter and the radiofrequency ablation apparatus can also be used for neuroablation in other blood vessels or tracheae like pelvis and pulmonary artery. It should be noted that the radiofrequency ablation catheter provided by the present invention is not limited to the applications listed above, but can be applied to neuroablation of other portions.

Above is the introduction of the radiofrequency ablation catheter provided by the present invention, and the present invention also provides a radiofrequency ablation apparatus comprising the radiofrequency ablation catheter. Besides the corrugated radiofrequency ablation catheter, the radiofrequency ablation apparatus also comprises a radiofrequency ablation main unit connected with the radiofrequency ablation catheter. The supporting, wall-attaching adjustment wire and the wall-attaching adjustment wire inside the electrode frame are correspondingly connected to the control handle after running through the connecting catheter, and the shape of the electrode frame can be changed by pulling the wall-attaching adjustment wire through the control handle, so that the electrode frame can be well attached to the wall in target lumens with different diameters. Furthermore, the radiofrequency cables and the thermocouple wires in the electrode frame are connected to corresponding circuits in the radiofrequency ablation main unit respectively through the connecting catheter, so that the radiofrequency ablation main unit can conduct radiofrequency control and temperature monitoring on the multiple electrodes. The arrangement of the control handle and the radiofrequency ablation main unit can be found in previous published patent applications of the applicant, and the descriptions of specific structures thereof are omitted herein.

Above is detailed description of the corrugated radiofrequency ablation catheter and the apparatus thereof provided by the present invention. For those skilled in the art, any apparent modifications without deviating from the spirit of the present invention will fall within the protection scope of the present invention.

What is claimed is:

1. A corrugated radiofrequency ablation catheter, provided with a strip-shaped connecting catheter, an electrode frame provided at a front extremity of the connecting catheter, and a control handle provided at a rear extremity of the connecting catheter; characterized in that:
   the electrode frame is a corrugated electrode frame comprising multiple corrugations, where multiple electrodes are distributed on each of the multiple corrugations;
   a slidable, supporting, wall-attaching adjustment wire is provided within one lumen of the electrode frame and the connecting catheter, and the supporting, wall-attaching adjustment wire is divided into a flexible segment away from the control handle and a rigid segment in proximity to the control handle; a head end of the supporting, wall-attaching adjustment wire is limited outside a front extremity of the electrode frame, and can slide relative to the front extremity of the electrode frame; a tail end of the supporting, wall-attaching adjustment wire is fixed to a control element arranged on the control handle or arranged externally, and the control element is used for controlling the supporting, wall-attaching adjustment wire to move forward and backward;
   when the rigid segment of the supporting, wall-attaching adjustment wire is in the electrode frame, a portion, which overlaps with the rigid segment, of the electrode frame is linear; and when the flexible segment of the supporting, wall-attaching adjustment wire is in the electrode frame, a portion which overlaps with the flexible segment, of the electrode frame is corrugated;
   a wall-attaching adjustment wire is further arranged, the wall-attaching adjustment wire is composed of two or more filaments, the multiple filaments are used for adjusting one corrugation or one segment of corrugations on the electrode frame respectively, one segment of corrugations comprises two or more corrugations, a front extremity of each filament is fixed to one end of corresponding corrugation/corrugated segment, and a rear extremity of each filament runs around the corresponding corrugation/corrugated segment, runs through the lumen in the electrode frame and the connecting catheter, and is then fixed to a corresponding control element provided on the control handle or arranged externally.

2. The corrugated radiofrequency ablation catheter according to claim 1, characterized in that:
   the flexible segment is made of a filament with diameter or rigidity smaller than that of the rigid segment, and the flexible segment and the rigid segment are integrally formed or assembled by means of two filaments with different diameters.

3. The corrugated radiofrequency ablation catheter according to claim 1, characterized in that:
   the flexible segment is of a spring structure or a hose structure.

4. The corrugated radiofrequency ablation catheter according to claim 1, characterized in that:
   the flexible segment and the rigid segment of the supporting, wall-attaching adjustment wire are made of one piece of rigid material, wherein a front segment of the rigid material is provided with grooves and/or holes so as to form the flexible segment; or
   the flexible segment and the rigid segment of the supporting, wall-attaching adjustment wire are made of one piece of flexible material, wherein the rigid segment is formed by assembling an outer sleeve on a rear segment.

5. The corrugated radiofrequency ablation catheter according to claim 1, characterized in that:
   the multiple corrugations constituting the electrode frame are arranged from the front extremity to the rear extremity of the electrode frame in, a size increasing mode, or the multiple corrugations constituting the electrode frame are arranged from the front extremity to the rear extremity of the electrode frame in a size reducing mode.

6. The corrugated radiofrequency ablation catheter according to claim 1, characterized in that:
   a developing head configured to image is arranged at the head end of the supporting, wall-attaching adjustment wire.

7. The corrugated radiofrequency ablation catheter according to claim 1, characterized in that:
   the front extremity of the wall-attaching adjustment wire is fixed to the supporting, wall-attaching adjustment wire.

8. The corrugated radiofrequency ablation catheter according to claim 1, characterized in that:
   the corrugated radiofrequency ablation catheter further comprises a shaping wire arranged within the electrode frame.

9. The corrugated radiofrequency ablation catheter according to claim 1, characterized in that:
   the wall-attaching adjustment wire is eccentrically provided on the electrode frame.

10. A radiofrequency ablation apparatus, characterized by comprising the radiofrequency ablation catheter according to claim 1, and a radiofrequency ablation main unit connected with the radiofrequency ablation catheter.

\* \* \* \* \*